United States Patent
Zhu et al.

(10) Patent No.: US 11,192,833 B2
(45) Date of Patent: Dec. 7, 2021

(54) PROCESSES AND APPARATUSES FOR TOLUENE AND BENZENE METHYLATION IN AN AROMATICS COMPLEX

(71) Applicant: UOP LLC, Des Plaines, IL (US)

(72) Inventors: Guanghui Zhu, Mount Prospect, IL (US); Steven A. Bradley, Arlington Heights, IL (US); Mitchell J. Kowalczyk, Brookfield, IL (US); Gregory B. Kuzmanich, Arlington Heights, IL (US); Joseph A. Montalbano, Elmhurst, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/377,798

(22) Filed: Apr. 8, 2019

(65) Prior Publication Data

US 2020/0002245 A1    Jan. 2, 2020

Related U.S. Application Data

(60) Provisional application No. 62/690,851, filed on Jun. 27, 2018.

(51) Int. Cl.
*C07C 2/64* (2006.01)
*B01J 19/00* (2006.01)
*B01J 19/02* (2006.01)
*C07C 15/08* (2006.01)

(52) U.S. Cl.
CPC ............. *C07C 2/64* (2013.01); *B01J 19/0013* (2013.01); *B01J 19/02* (2013.01); *B01J 2219/00051* (2013.01); *B01J 2219/00162* (2013.01); *C07C 15/08* (2013.01)

(58) Field of Classification Search
CPC . C07C 2/64; C07C 2/864; C07C 15/08; B01J 19/0013; B01J 19/02; B01J 2219/00051; B01J 2219/00162
See application file for complete search history.

(56) References Cited

U.S. PATENT DOCUMENTS

| | | | |
|---|---|---|---|
| 3,182,094 A | | 5/1965 | Glazier et al. |
| 5,849,969 A | * | 12/1998 | Heyse .................. B01J 19/0026 585/483 |
| 7,763,766 B2 | * | 7/2010 | Bozzano ................ B01J 8/0055 208/48 AA |
| 7,887,776 B2 | * | 2/2011 | Finkelshtein ............ C01D 5/02 423/482 |
| 8,119,203 B2 | | 2/2012 | Hise et al. |
| 2016/0264495 A1 | * | 9/2016 | Molinier ................ B01D 3/141 |

FOREIGN PATENT DOCUMENTS

| | | | |
|---|---|---|---|
| CN | 104150927 A | | 11/2014 |
| CN | 104150927 B | * | 9/2016 |
| CN | 106854128 A | | 6/2017 |
| WO | 2018057125 A2 | | 3/2018 |

OTHER PUBLICATIONS

Ghattas ("Oxidative Dehydrogenation of Methanol on Chromium Oxide/Montmorillonite K10 Catalysts" Petroleum Science and Technology, 2006, 24:12, 1381-1394, DOI: 10.1080/10916460500294937) (Year: 2006).*
Inokawa et al (2018 IOP Conf. Ser.: Mater. Sci. Eng. 458 012018) (Year: 2018).*
Mensch ("The Oxidation of Methanol on Cr2O3 (1012) Single Crystal Surfaces" https://vtechworks.lib.vt.edu/handle/10919/31546) (Year: 2003).*
Saint-Gobain ("Chemical Processing Refractory System" https://web.archive.org/web/20170701104137/http://www.refractories.saint-gobain.com/markets/petrochemistry-chemical-processing. publicly available on Jul. 1, 2017) (Year: 2017).*
Holstein ("Effect of Oxidizing and Reducing Gas Atmosphere on the Iron-Catalyzed Formation of Filamentous Carbon from Methanol" Ind. Eng. Chem. Res. 1994, 33, 1363-1372) (Year: 1994).*
Bases ("Understanding Refractory Failure—A New Perspective" https://insulation.org/io/articles/understanding-refractory-failure-a-new-perspective/ Aug. 1, 2006) (Year: 2006).*
Doshi ("Overview of Saint-Gobain and Introduction to Refractory Solutions for Gasification" https://missionenergy.org/gasification2017/presentation/SaintGobain.pdf) (Year: 2017).*
Hoyt et al. ("High Temperature Metal Deterioration In Atmospheres Containing Carbon-Monoxide and Hydrogen" Corrosion (1959) 15 (12): Abstract) (Year: 1959).*
International Search Report from PCT application No. PCT/US2019/038613, dated Sep. 26, 2019.
Written Opinion from PCT application No. PCT/US2019/038613, dated Sep. 11, 2019.
Examination Report for corresponding Indian Application No. 202017053128 dated Mar. 2, 2021.

\* cited by examiner

*Primary Examiner* — In Suk C Bullock
*Assistant Examiner* — Jason Y Chong

(57) ABSTRACT

This present disclosure relates to processes and apparatuses for toluene and benzene methylation in an aromatics complex for producing paraxylene. More specifically, the present disclosure relates to processes and apparatuses for toluene and benzene methylation within an aromatics complex for producing paraxylene wherein an embodiment uses a reactor having a refractory comprising a low iron content refractory.

8 Claims, No Drawings

PROCESSES AND APPARATUSES FOR TOLUENE AND BENZENE METHYLATION IN AN AROMATICS COMPLEX

RELATED APPLICATIONS

This application claims priority to U.S. Provisional Patent Application Ser. No. 62/690,851 filed Jun. 27, 2018, the entirety of which is hereby incorporated by reference.

FIELD

This present disclosure relates to processes and apparatuses for toluene and benzene methylation in an aromatics complex for producing paraxylene. More specifically, the present disclosure relates to processes and apparatuses for toluene and benzene methylation within an aromatics complex for producing paraxylene wherein an embodiment uses a reactor having a refractory comprising a low iron refractory.

BACKGROUND

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated or transalkylated to yield benzene and $C_8$ aromatics from which the individual xylene isomers are recovered.

An aromatics complex flow scheme has been disclosed by Meyers in the Handbook of Petroleum Refining Processes, 2d. Edition in 1997 by McGraw-Hill, and is incorporated herein by reference.

Traditional aromatics complexes send toluene to a transalkylation zone to generate desirable xylene isomers via transalkylation of the toluene with $A_{9+}$ components. $A_{9+}$ components are present in both the reformate bottoms and the transalkylation effluent.

Paraxylene is most often produced from a feedstock which has a methyl to phenyl ratio of less than 2. As a result, the paraxylene production is limited by the available methyl groups in the feed. In addition, paraxylene production also typically produces benzene as a byproduct. Since paraxylene is more valuable than benzene and the other byproducts produced in an aromatics complex, there is a desire to maximize the paraxylene production from a given amount of feed.

Toluene methylation or benzene methylation processes use iron or iron-based alloys as reactor materials. Iron can catalyze the hydrocarbon to form filamentous carbon and thus plug the reactors. Additionally, iron can be corroded through a process called metal dusting when hydrocarbon presents. Coke formation and metal dusting reduce reactor life time and add cost to process operation. The impact can be minimized by lowering the process temperature but this could also bring down the catalyst activity. For fluidized bed, a refractory layer was typically applied inside the vessel to protect metal wall from abrasion. The refractories usually contains some level of iron. When exposed to methanol at 600 C, the iron can also form metal catalyzed cork and pulverize refractory into small particles. In other cases, if coking is so extreme, the refractory can peel away from the wall and fall into the reactor damaging the internals. This is referred to as 'jacking'. In such case, the refractory cannot be effective any more and may damage other reactor internals.

SUMMARY

The present subject matter relates to processes and apparatuses for toluene methylation in an aromatics complex for producing paraxylene. More specifically, the present disclosure relates to processes and apparatuses for toluene methylation within an aromatics complex for producing paraxylene wherein a layer of special refractory material has been applied to the internal wall of the reactor. This invention proposes to apply a layer of special refractory materials on the reactor internal wall. The refractory materials has low iron content (less than 0.1 wt %); therefore the coke formation can be dramatically reduced. Additionally, the layer of refractory materials can act as thermal barrier to allow the metal wall stay at lower temperature than the process temperature, thus to further reduce the coke formation on the wall. This can be applied to both fixed bed reactor and fluidized bed reactor.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

DEFINITIONS

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

DETAILED DESCRIPTION

The following description is not to be taken in a limiting sense, but is made merely for the purpose of describing the general principles of exemplary aspects. The scope of the present disclosure should be determined with reference to the claims.

The claimed invention comprises a first embodiment wherein a toluene methylation process or apparatus for alkylating an aromatic hydrocarbon reactant with an alkylating reagent comprising methanol to produce an alkylated aromatic product, comprising a reactor having a refractory. The refractory lines the inside of the toluene methylation reactor. This invention proposes to apply a layer of special refractory materials on the reactor internal wall. The refractory materials has low iron content (less than 0.1 wt %); therefore the coke formation can be dramatically reduced. Additionally, the layer of refractory materials can act as thermal barrier to allow the metal wall stay at lower temperature than the process temperature, thus to further reduce the coke formation on the wall. This can be applied to both fixed bed reactor and fluidized bed reactor. The reactor comprises a temperature of about 500° C. to about 700° C. The reactor comprises an operating bed density of about 0.05 kg/m3 to 0.29 kg/m3. The weight hourly space velocity of the reactor is about 4 hr-1 to about 20 hr-1. The reactor may operate at a pressure of about 1 barg to about 10 barg. The mixed oxide can be applied to a holding structure which is attached to the internal reactor wall. Afterwards the mixed oxide goes through drying and firing process to become rigid and abrasion resistant.

It should be noted that various changes and modifications to the presently preferred embodiments described herein will be apparent to those skilled in the art. Such changes and modifications may be made without departing from the spirit and scope of the present subject matter and without diminishing its attendant advantages.

SPECIFIC EMBODIMENTS

While the following is described in conjunction with specific embodiments, it will be understood that this description is intended to illustrate and not limit the scope of the preceding description and the appended claims.

A first embodiment of the invention is a process for alkylating an aromatic hydrocarbon reactant with an alkylating reagent comprising methanol to produce an alkylated aromatic product, comprising introducing the aromatic hydrocarbon into a reactor having an inner refractory lining having a low iron content; and recovering the alkylate aromatic product, produced by reaction of the aromatic reactant and the alkylating reagent, from the reactor. An embodiment of the invention is one, any or all of prior embodiments in this paragraph up through the first embodiment in this paragraph, wherein the aromatic hydrocarbon reactant includes toluene, the alkylating reagent includes methanol, and the alkylated aromatic product includes xylene. An embodiment of the invention is one, any or all of prior embodiments in this paragraph up through the first embodiment in this paragraph, wherein the aromatic hydrocarbon reactant includes benzene, the alkylating reagent includes methanol, and the alkylated aromatic product includes xylene. An embodiment of the invention is one, any or all of prior embodiments in this paragraph up through the first embodiment in this paragraph, wherein the reactor operates at a temperature of about 500° C. to about 700° C. An embodiment of the invention is one, any or all of prior embodiments in this paragraph up through the first embodiment in this paragraph, wherein the reactor operates at a pressure of about 1 barg to about 10 barg. An embodiment of the invention is one, any or all of prior embodiments in this paragraph up through the first embodiment in this paragraph, wherein the entire inside lining of the reactor is coated with the refractory. An embodiment of the invention is one, any or all of prior embodiments in this paragraph up through the first embodiment in this paragraph, wherein the refractory comprises a low iron content between about 0.0001 wt % to about 0.5 wt % iron. An embodiment of the invention is one, any or all of prior embodiments in this paragraph up through the first embodiment in this paragraph, wherein the refractory comprises a low iron content between about 0.0001 wt % to about 0.15 wt % iron. An embodiment of the invention is one, any or all of prior embodiments in this paragraph up through the first embodiment in this paragraph, further comprising adding water to the reactor.

A second embodiment of the invention is an apparatus for alkylating an aromatic hydrocarbon reactant with an alkylating reagent comprising methanol to produce an alkylated aromatic product, comprising a line comprising the aromatic hydrocarbon in upstream communication with a reactor having an inner refractory lining; and a line in downstream communication with the reactor comprising the alkylate aromatic product, produced by reaction of the aromatic reactant and the alkylating reagent, from the reactor. An embodiment of the invention is one, any or all of prior embodiments in this paragraph up through the second embodiment in this paragraph, wherein the aromatic hydrocarbon reactant includes toluene, the alkylating reagent includes methanol, and the alkylated aromatic product includes xylene. An embodiment of the invention is one, any or all of prior embodiments in this paragraph up through the second embodiment in this paragraph, wherein the aromatic hydrocarbon reactant includes benzene, the alkylating reagent includes methanol, and the alkylated aromatic product includes xylene. An embodiment of the invention is one, any or all of prior embodiments in this paragraph up through the second embodiment in this paragraph, wherein the reactor operates at a temperature of about 500° C. to about 700° C. An embodiment of the invention is one, any or all of prior embodiments in this paragraph up through the second embodiment in this paragraph, wherein the reactor operates at a pressure of about 1 barg to about 10 barg. An embodiment of the invention is one, any or all of prior embodiments in this paragraph up through the second embodiment in this paragraph, wherein the entire inside lining of the reactor is coated with the refractory. An embodiment of the invention is one, any or all of prior embodiments in this paragraph up through the second embodiment in this paragraph, wherein the refractory comprises a low iron content between about 0.0001 wt % to about 0.5 wt % iron. An embodiment of the invention is one, any or all of prior embodiments in this paragraph up through the second embodiment in this paragraph, wherein the refractory comprises a low iron content between about 0.0001 to about 0.15 wt % iron. An embodiment of the invention is one, any or all of prior embodiments in this paragraph up through the second embodiment in this paragraph, further comprising an addition line in upstream communication with the reactor comprising water.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

The invention claimed is:

1. A process for alkylating an aromatic hydrocarbon reactant with an alkylating reagent comprising methanol to produce an alkylated aromatic product, comprising:

introducing the aromatic hydrocarbon reactant and the alkylating reagent into a reactor to produce the alkylated aromatic product, wherein the reactor has an inner refractory lining having an iron content of from about 0.0001 wt % to about 0.5 wt % iron; and recovering the alkylated aromatic product from the reactor, wherein the alkylated aromatic product comprises xylene.

2. The process of claim 1, wherein the aromatic hydrocarbon reactant comprises toluene.

3. The process of claim 1, wherein the aromatic hydrocarbon reactant comprises benzene.

4. The process of claim 1, wherein the reactor operates at a temperature of about 500° C. to about 700° C.

5. The process of claim 1, wherein the reactor operates at a pressure of about 1 barg to about 10 barg.

6. The process of claim 1, wherein an entire inside lining of the reactor is coated with the inner refractory lining.

7. The process of claim 1, wherein the iron content is from about 0.0001 wt % to about 0.15 wt % iron.

8. The process of claim 1, further comprising adding water to the reactor.

* * * * *